United States Patent [19]
Blatt et al.

[11] Patent Number: 5,968,839
[45] Date of Patent: Oct. 19, 1999

[54] METHOD AND DEVICE PRODUCING A PREDETERMINED DISTRIBUTION OF DETECTABLE CHANGE IN ASSAYS

[75] Inventors: Joel M. Blatt, Palo Alto; Michael P. Allen, Los Altos; Paul J. Patel, Sunnyvale, all of Calif.

[73] Assignee: Metrika, Inc., Sunnyvale, Calif.

[21] Appl. No.: 08/645,453

[22] Filed: May 13, 1996

[51] Int. Cl.$^6$ ............................................. G01N 33/563
[52] U.S. Cl. ............................ 436/513; 436/169; 435/11
[58] Field of Search .................................. 436/513, 514, 436/169; 435/11

[56] References Cited

U.S. PATENT DOCUMENTS

| | | | |
|---|---|---|---|
| 4,038,485 | 7/1977 | Johnston et al. | 435/4 |
| 4,094,647 | 6/1978 | Deutsch et al. | 23/255 TP |
| 4,160,008 | 7/1979 | Fenocketti et al. | 422/56 |
| 4,168,146 | 9/1979 | Grubb et al. | 23/230 B |
| 4,224,439 | 9/1980 | Ayers et al. | 536/32 |

(List continued on next page.)

FOREIGN PATENT DOCUMENTS

| | | | |
|---|---|---|---|
| 0415298 | 3/1991 | European Pat. Off. | G01N 33/92 |
| 0421294 | 4/1991 | European Pat. Off. | G01N 33/543 |
| 0516095 | 5/1992 | European Pat. Off. | |
| 8000173 | 1/1980 | Netherlands | G01N 33/54 |
| 8102790 | 10/1981 | WIPO | G01N 27/26 |
| 8808534 | 11/1988 | WIPO . | |
| 9010869 | 9/1990 | WIPO | G01N 33/52 |
| 9114942 | 10/1991 | WIPO | G01N 31/22 |
| 9201498 | 2/1992 | WIPO . | |

OTHER PUBLICATIONS

A Dot–Immunobinding Assay for Monoclonal and Other Antibodies, Richard Hawkes, Evelyn Niday, and Julian Gordon, Analytical Biochemistry 119, pp. 142–147 (1982).

Detection of Specific Hybridoma Clones by Replica Immunoadsorption of Their Secreted Antibodies, Jacqueline Sharon, Sherie L. Morrison, and Elvin A. Kabat, Dec. 7, 1978, Proc. Natl. Acad. Sci. USA vol. 76, No. 3, pp. 1420–1424 Mar. 1979.

Home Cholesterol Testing, Editorial, The Lancet, vol. 340, Dec. 5, 1992 No. 8832, p. 1386.

Reliability and Feasibility of Pregnancy Home–Use Tests: Laboratory Validation and Diagnostic Evaluation by 638 Volunteers, Joelle Daviaud, Dominique Fournet, Chantal Ballongue, Guy–Pierre Guillem, Alain Leblanc, Claude Casellas, and Bernard Pau, Clin. Chem. 39/1, 53–59 (1993).

A Multilayaer Membrane System for Blood Plasma Isolation for Use in Primary Health Care, APM Van Oudheusden and HDW Roesink, Ann Clin Biochem 1991; 28: 55–59.

(List continued on next page.)

*Primary Examiner*—James C. Housel
*Assistant Examiner*—Ginny Allen Portner
*Attorney, Agent, or Firm*—Timothy H. Gens; Trial & Technology Law Group

[57] ABSTRACT

A transport matrix and diagnostic device are provided which produce a physically detectable change in a predetermined distribution across a detection zone which correlates with the amount of selected analyte in a sample. The matrix includes a detection zone having a capture reagent yielding a physically detectable change which correlates with the amount of selected analyte in the sample. The detection zone has a leading boundary which first encounters the sample and a trailing boundary which encounters the sample after being transported across the detection zone. The capture reagent is immobilized on the matrix in a predetermined distribution from the leading boundary to the trailing boundary of the detection zone. A method is also provided which determines the level of a selected analyte in a sample by distributing a physically detectable change in a predetermined pattern across a detection zone on a transport matrix which correlates with the amount of selected analyte.

45 Claims, 3 Drawing Sheets

U.S. PATENT DOCUMENTS

| | | |
|---|---|---|
| 4,233,402 | 11/1980 | Maggio et al. . |
| 4,235,601 | 11/1980 | Deutsch et al. .................. 23/230 R |
| 4,275,149 | 6/1981 | Litman et al. . |
| 4,281,061 | 7/1981 | Zuk et al. .............................. 435/188 |
| 4,313,734 | 2/1982 | Leuvering ............................ 23/230 B |
| 4,361,537 | 11/1982 | Deutsch et al. ....................... 422/56 |
| 4,366,241 | 12/1982 | Tom et al. . |
| 4,373,932 | 2/1983 | Gribnau ................................. 436/501 |
| 4,376,110 | 3/1983 | David et al. ........................... 436/513 |
| 4,435,504 | 3/1984 | Zuk et al. . |
| 4,446,232 | 5/1984 | Liotta . |
| 4,452,901 | 6/1984 | Gordon et al. ......................... 436/506 |
| 4,517,288 | 5/1985 | Giegel et al. . |
| 4,552,839 | 11/1985 | Gould et al. . |
| 4,627,445 | 12/1986 | Garcia et al. .......................... 128/770 |
| 4,637,403 | 1/1987 | Garcia et al. .......................... 128/770 |
| 4,703,017 | 10/1987 | Campbell et al. ..................... 436/501 |
| 4,734,360 | 3/1988 | Phillips .................................. 435/25 |
| 4,740,468 | 4/1988 | Weng et al. . |
| 4,756,828 | 7/1988 | Litman et al. . |
| 4,756,884 | 7/1988 | Hillman et al. ........................ 422/73 |
| 4,757,004 | 7/1988 | Houts et al. . |
| 4,774,192 | 9/1988 | Terminiello .......................... 436/530 |
| 4,787,398 | 11/1988 | Garcia et al. .......................... 128/770 |
| 4,855,240 | 8/1989 | Rosenstein et al. ................... 436/514 |
| 4,861,711 | 8/1989 | Friesen .................................. 436/7.92 |
| 4,868,108 | 9/1989 | Bahar et al ........................... 435/7.92 |
| 4,883,688 | 11/1989 | Houts et al. ........................... 427/285 |
| 4,945,205 | 7/1990 | Litman et al. ..................... 219/121.72 |
| 4,956,302 | 9/1990 | Gordon et al. ......................... 436/161 |
| 4,999,287 | 3/1991 | Allen et al. ............................ 435/11 |
| 5,026,653 | 6/1991 | Lee et al. .............................. 436/518 |
| 5,030,558 | 7/1991 | Litman et al. ......................... 435/7.91 |
| 5,036,000 | 7/1991 | Palmer .................................. 435/26 |
| 5,075,078 | 12/1991 | Osikowicz et al. .................... 422/56 |
| 5,087,556 | 2/1992 | Ertinghausen ......................... 435/7.9 |
| 5,096,837 | 3/1992 | Fan et al. .............................. 436/514 |
| 5,114,350 | 5/1992 | Hewett .................................. 435/288 |
| 5,132,086 | 7/1992 | Allen et al. ............................ 422/56 |
| 5,132,806 | 7/1992 | Allen et al. ............................ 42/56 |
| 5,155,025 | 10/1992 | Allen et al. ............................ 435/11 |
| 5,160,486 | 11/1992 | Schapfenbacher et al. ............ 422/56 |
| 5,171,688 | 12/1992 | Hewett et al. ......................... 435/11 |
| 5,202,268 | 4/1993 | Kuhn et al. ........................... 436/525 |
| 5,212,060 | 5/1993 | Maddox ................................ 435/7.1 |
| 5,213,965 | 5/1993 | Jones .................................... 435/11 |
| 5,223,219 | 6/1993 | Subramanian et al. ................ 422/55 |
| 5,223,220 | 6/1993 | Fan et al. .............................. 422/58 |
| 5,234,813 | 8/1993 | McGeehan et al. ................... 435/7.9 |
| 5,340,539 | 8/1994 | Allen et al. ............................ 422/56 |
| 5,354,692 | 10/1994 | Yang et al. ............................ 436/514 |
| 5,356,785 | 10/1994 | McMahon et al. .................... 435/7.92 |
| 5,416,000 | 5/1995 | Allen et al. ............................ 435/7.92 |
| 5,424,193 | 6/1995 | Pronovost et al. .................... 435/7.32 |
| 5,426,030 | 6/1995 | Rittersdorf et al. .................... 435/11 |
| 5,451,504 | 9/1995 | Fitzpatrick ............................ 435/7.2 |
| 5,580,794 | 12/1996 | Allen .................................... 436/169 |
| 5,602,040 | 2/1997 | May ..................................... 436/514 |

OTHER PUBLICATIONS

Instrument–Free Quantitative Test Systems, Michael P. Allen and Prithipal Singh, Applications of Diagnostics, pp. 147–176 (1990).

Zourlas, PA et al, Clin. Exp. Obstet Gynocol, 1992, vol. 19(3), pp. 180–188.

METHOD AND DEVICE PRODUCING A PREDETERMINED DISTRIBUTION OF DETECTABLE CHANGE IN ASSAYS

RELATED APPLICATIONS

The subject matter of this application is related to a disposable single-use digital electronic instrument that is entirely self-contained, including all chemistry reagents, as disclosed in U.S. application Ser. No. 08/111,347 entitled "Novel Disposable Electronic Assay Device" filed Aug. 24, 1993 by Michael P. Allen and now abandoned, U.S. application Ser. No. 08/455,236 entitled "Novel Disposable Electronic Assay Device" filed May 31, 1995 by Michael P. Allen, U.S. application Ser. No. 08/512,844 entitled "Dry Reagent Particle Assay And Device Having Multiple Test Zones And Method Therefor" filed Aug. 9, 1995 by Joel M. Blatt and Michael P. Allen, and U.S. application Ser. No. 08/642,228 filed Apr. 30, 1996 by Raymond T. Hebert et al. The above applications have the same assignee as the present invention and are incorporated herein by reference in their entirety.

FIELD OF THE INVENTION

The present invention relates to a method and device which varies the capture efficiency across a zone for detecting a physical change on the surface of a sample-exposed analytical chemistry strip in a diagnostic device which displays medical information.

BACKGROUND OF THE INVENTION

In the past, immunoassays were developed for the quantitative and qualitative determination of a wide variety of compounds in a laboratory setting using detailed procedures and expensive instrumentation. Recent developments in immunodiagnostics have resulted in a movement toward more simple approaches to the rapid analysis of clinical samples. The development of solid phase bound reagents has eliminated the need for precipitation in the separation of bound reagents from free reagents. Further advancements in solid phase immunochemistry have resulted in non-instrumented dry reagent strip immunoassays. This configuration allows for the visual qualitative or semi-quantitative determination of analytes in patient samples without the use of an instrument.

There are two basic types of non-instrumented immunoassay configurations. In the first type, or visual color zone type, a signal is generated at a specific zone on the strip where the signal indicates the presence of analyte, and the intensity of the signal indicates the concentration of the analyte in the sample. This type of assay requires visual color interpretation either for the presence of color above a threshold, as in the case of a qualitative test, or the comparison of the color intensity to a color chart, as in the case of a semi-quantitative test. In the second type, the visual signal is produced along the length of a bibulous assay strip. During wicking, the analyte reacts with a signal-producing reagent and forms a visible signal along the support. The migration distance of the signal from the proximal end of the strip is a direct measure of analyte concentration. This type of non-instrumented migration height assay can achieve quantitative results with reasonable performance.

Although these single use, thermometer-type, non-instrumented quantitative devices and non-instrumented color comparison devices for qualitative measurement have shown adequate performance, they have several problems associated with reliability and convenience. The colors generated on these devices are not always uniform and sharp. In the case of migration type assays the border is often light in color, unclear and difficult to read. This translates directly into user errors since the user must make a judgment related to the position of the color band border. In the case of non-instrumented pregnancy tests it is sometimes difficult to visually interpret the intensity of the colored spot (especially at HCG concentrations close to the cut-off sensitivity), and interpretation of the result is sometimes a problem. Any time a non-technical operator is required to make a visual judgment or interpretation, an error is possible, and sometimes, is unavoidable.

To improve the accuracy and reliability of assay results, several qualitative and quantitative diagnostic tests have been developed in the clinical field utilizing a reflectometer for measuring optical radiation reflected from a test element such as a zone of detection on an analytical chemistry strip. Reflectometers have been constructed featuring optical arrangements of lenses, filters, apertures, a radiation source, and detector. Examples are described in U.S. Pat. Nos. 4,219,529, 4,224,032 and 3,536,927.

Often, problems arise with obtaining accurate and precise measurements of the diffusely reflected optical radiation from the surface of the assay strip within the sampling area or detection zone. One of the causes is that the physically detectable change which is being measured does not occur uniformly across the test area. A lateral flow assay strip passes a signal reagent through the detection zone which contains an immobilized capture reagent. The signal reagent first encounters and immediately begins binding with a substantial portion, if not the entire amount, of the capture reagent at the leading boundary of the detection zone. The result is a significantly higher signal intensity in a narrow region at the leading boundary, with a rapidly decreasing intensity towards the trailing boundary of the detection zone. Overall, the signal intensity is distributed in a non-uniform gradient across the detection zone.

Another potential cause of inaccurate measurements is high analyte concentrations which can produce a decrease in signal intensity or "hook effect." When the analyte concentration is significantly greater than the capture reagent concentration, the signal intensity can actually decrease, falsely indicating an acceptable assay result.

There is a need to achieve substantially uniform distribution of a physically detectable change across a detection zone using a capture reagent or other signal producing reagent. Another need is to achieve a predetermined distribution of the physically detectable change in the detection zone of an assay strip. These needs have not been filled by the prior art.

Thus, a need exists in the field of diagnostics for a method and device which varies the capture efficiency across a zone for detecting a physical change on the surface of a sample-exposed analytical chemistry strip. The uniform or predetermined distribution should be sufficiently inexpensive, timely, efficient, durable, and reliable for use in a diagnostic device which permits point-of-care use by untrained individuals in locations such as the home, sites of medical emergencies, or locations other than a clinic.

SUMMARY OF THE INVENTION

The present invention provides a transport matrix producing a physically detectable change in a predetermined distribution across a detection zone which correlates with the amount of selected analyte in a sample. The matrix includes a detection zone having a capture reagent yielding a physically detectable change which correlates with the amount of selected analyte in the sample. The detection zone has a leading boundary which first encounters the sample and a trailing boundary which encounters the sample after being transported across the detection zone. The capture reagent is immobilized on the matrix in a predetermined distribution from the leading boundary to the trailing boundary of the detection zone.

The present invention also provides a transport matrix for determining the presence of selected analyte in a sample. The matrix includes a detection zone having a capture reagent yielding a physically detectable change which correlates with the amount of selected analyte in the sample. The physically detectable change is immobilized in an approximately uniform distribution across the detection zone.

An embodiment of the present invention provides a transport matrix producing a physically detectable change with a signal producing conjugate in a predetermined distribution across a detection zone which correlates with the amount of selected analyte in a sample. The matrix includes a detection zone having a capture reagent yielding a physically detectable change which correlates with the amount of selected analyte in the sample. The detection zone has a leading boundary which first encounters the sample and a trailing boundary which encounters the sample after being transported across the detection zone. The capture reagent is immobilized in a predetermined distribution approximately uniform from the leading boundary to the trailing boundary of the detection zone. A zone is located prior to the leading edge of the detection zone which has a blocking reagent diffusively immobilized therein. The blocking reagent is capable of diffusing across the detection zone and modifying the capture efficiency of the approximately uniform distribution of the capture reagent to form an approximately uniform capture efficiency across the detection zone.

Another embodiment of the present invention provides a transport matrix as described above which includes a diffusion control material distributed within the detection zone. The diffusion control material slowing the transportation of the sample across the detection zone and increasing capture efficiency of the capture reagent from the leading edge to the trailing edge.

One preferred embodiment of the present invention provides a transport matrix producing a physically detectable change in a predetermined distribution across a plurality of detection zones which correlates with the amount of selected analyte in a sample. The matrix includes a first and a second detection zone. Each detection zone has a non-diffusively immobilized capture reagent yielding a physically detectable change which correlates with the amount of selected analyte in the sample. Each detection zone has a leading boundary which first encounters the sample and a trailing boundary which encounters the sample after being transported across each detection zone. The capture reagent is immobilized in a predetermined distribution from the leading boundary to the trailing boundary of each detection zone.

Another preferred embodiment of the present invention is a diagnostic device for determining the presence of a selected analyte in a sample. The device includes a housing having an exterior surface and sealing an interior area. A receptor is configured to receive the sample containing an analyte selected for determining its presence. The receptor is located on the exterior surface of the housing. At least one transport matrix reacts the sample with a capture reagent to yield a physically detectable change in a detection zone which correlates with the amount of selected analyte in the sample. The detection zone has a leading boundary which first encounters the sample and a trailing boundary which encounters the sample after being transported across the detection zone. The capture reagent is immobilized in a predetermined distribution from the leading boundary to the trailing boundary of the detection zone.

The present invention also provides a method for determining the level of a selected analyte in a sample which includes the step of distributing a physically detectable change in a predetermined pattern across a detection zone on a transport matrix which correlates with the amount of selected analyte.

The advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

The present invention may be utilized in either instrumented or non-instrumented assay devices. Examples of instrumented devices include the disposable single- and multiple-use digital electronic instruments and assay devices described in detail in the above-identified related applications previously incorporated by reference. The present invention provides for more accurate measurement, by either visual observation or instrumentation, of a physically detectable change corresponding to the amount of the selected analyte in one or more detection zones of an assay.

Figures 1, 2:
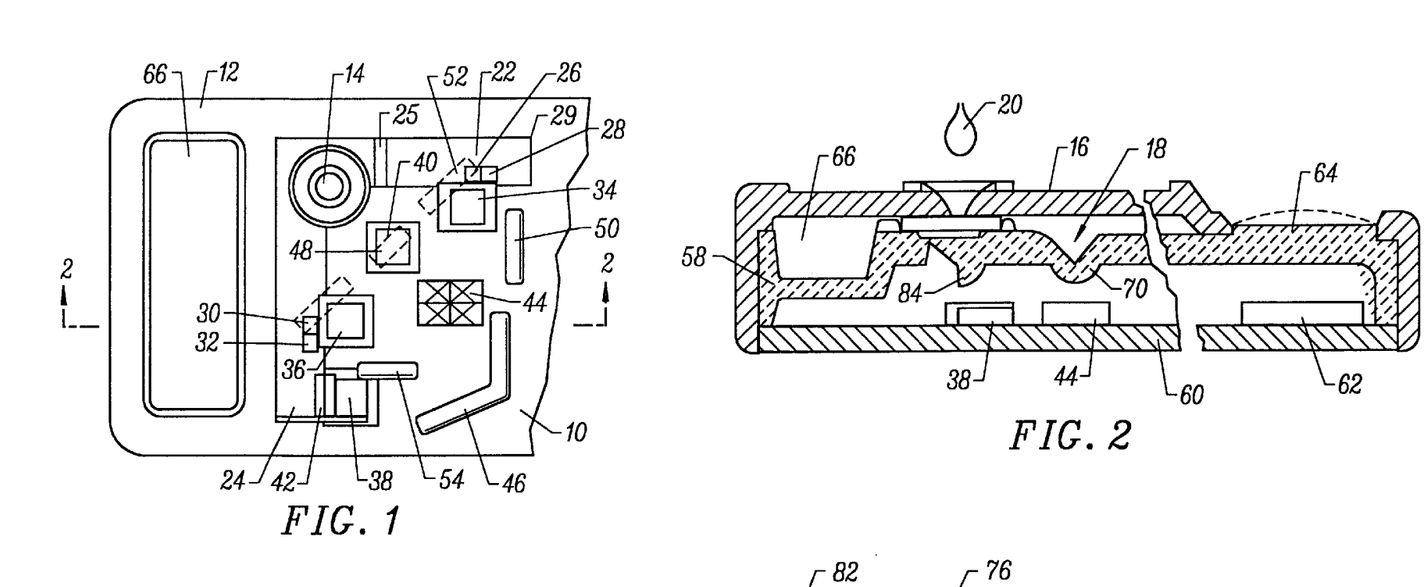
FIG. 1 is a partial top plan view of a diagnostic device having a portion cut-away to view the illumination and detection optics of the present invention.
FIG. 2 is a partial cross-sectional view of the diagnostic device illustrated in FIG. 1 along the lines 2—2.

One embodiment of an instrumented diagnostic device 10 having an analytical chemistry strip or transport matrix of the present invention is illustrated in FIGS. 1 and 2. The device 10 includes a housing 12 having a receptor such as an inlet port 14 which extends from the surface 16 of the housing to its interior 18 for receiving a sample 20 containing the one or more analytes to be determined. The inlet port 14 allows the sample 20 to be introduced to a first 22 and second transport matrix 24 containing chemical reagents for determining the presence of one or more selected analytes in the sample 20.

Once the sample 20 is introduced to both the first 22 and second 24 transport matrices through the inlet port 14, the sample 20 is chemically reacted with at least one reagent on each of the transport matrices 22, 24 to produce a reaction product mixture corresponding to the reagent. A portion of the reaction product mixture is transported to at least one detection zone on each of the transport matrices 22, 24 and produces a physically detectable change which correlates with the amount of the corresponding selected analyte in the sample 20.

As specifically illustrated in FIG. 1, each of the first 22 and second 24 transport matrices contains two detection zones 26, 28 and 30, 32 respectively. Detectors 34 are positioned to measure optical radiation reflected from the detection zones 26, 28 on the first transport matrix. Detectors 36 are positioned to measure optical radiation reflected from the detection zones 30, 32 on the second transport matrix. The quality control zone 42 does not exhibit the physically detectable change measured in each of the detection zones. Each of the detection zones and the quality control zone are examples of different types of sampling areas on the transport matrices where reflected optical radiation is sampled and measured by one of the detectors.

A light-emitting diode (LED) 44 provides a source of optical radiation which is directed to each detection zone 26, 28 and 30, 32 and the quality control zone 42 by a plurality of totally internal-reflecting elements (TIR) 46 which act as mirrors and as a consequence of the refractive index of the transparent material from which they are formed, require no reflective coating.

The illumination from the LED 44 is split four ways. A part of the illumination is directed to the reference detector 40 from the reflecting element 48. Another part of the illumination is directed to detection zones 26, 28 from a series of reflecting elements 50, 52. The illumination is also directed to detection zones 30, 32 from a series of reflecting elements 54, 56. The reflecting element 46 illuminates another sampling area on the second assay strip 24 for a quality control detector 38.

FIG. 2 specifically illustrates another view of the device with an optics assembly 58 and printed circuit board (PCB) 60 disposed within the interior 18 of the housing. The inlet port 14 leads to the first 22 and second 24 assay strips which are supported on the optics assembly 58. Each of the detectors 34, 36, 38, 40 and the LED 44 are mounted directly to the PCB 60. A liquid crystal display (LCD) 62 is also located on the PCB 60 and is positioned to direct its display through a window 64 or opening in the exterior of the housing 12. The LED 44, each of the detectors 36, and the LCD 62 are connected through the PCB 60. A pocket of desiccant 66 can be provided to prevent moisture from affecting the shelf life stability or the operation of the device 10.

Figure 3:
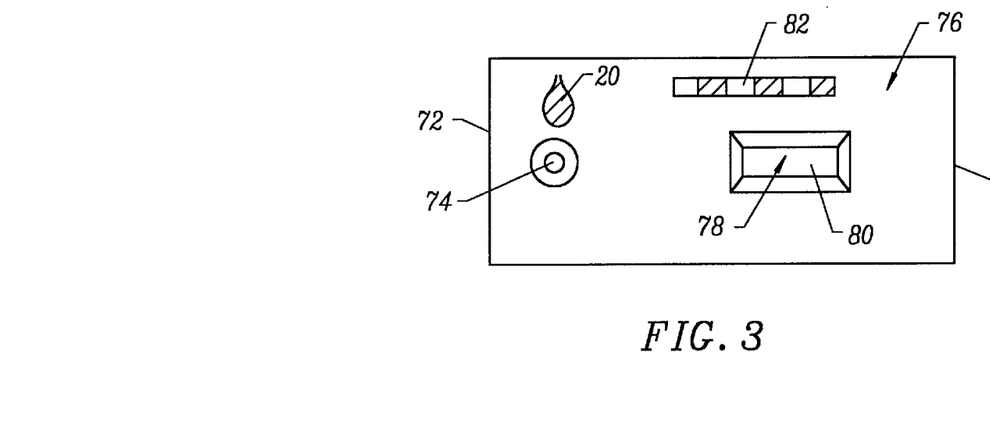
FIG. 3 is a top plan view of a non-instrumented diagnostic device using the present invention.

One embodiment of a non-instrumented diagnostic device 70 having an analytical chemistry strip or transport matrix of the present invention is illustrated in FIG. 3. The device 70 includes a housing 72 having a receptor such as an inlet port 74 which extends from the surface 76 of the housing to its interior for receiving the sample 20 containing one or more analytes to be determined. The inlet port 74 allows the sample 20 to be introduced to an assay strip 78 containing chemical reagents for determining the presence of one or more selected analytes in the sample 20.

Once the sample 20 is introduced to the assay strip 78 through the inlet port 74, the sample 20 is chemically reacted with at least one reagent on the assay strip 78 to produce a reaction product mixture corresponding to the reagent. A portion of the reaction product mixture is transported to at least one detection zone 80 on the assay strip and produces a physically detectable change which correlates with the amount of the corresponding selected analyte in the sample 20. The resulting color in the detection zone 80 can then be compared to a color bar 82 or other reference to visually determine the presence and concentration of the selected analyte.

The present invention varies the capture efficiency across a detection zone in the direction of sample flow on a transport matrix to achieve a uniform distribution or a varied, yet predetermined, distribution of the physically detectable change. Unless otherwise stated, the term across the detection zone shall mean in the direction of sample flow. The term detection zone shall mean the area measured, by either visual observation or by instruments, for the physically detectable change.

The term predetermined distribution as used herein can include any selected pattern, uniform or varied, across the detection zone. The term predetermined distribution also specifically includes the example where the distribution is generally uniform across the detection zone. It may be desired to vary the distribution of the physically detectable change across the detection zone. One reason for doing so is to compensate or correlate with the optics of a reflectometer having a varied or non-uniform sampling area.

The distribution of the physically detectable change is controlled by the distribution of a capture reagent. The capture reagent combines with a signal-producing reagent which can provide the physically detectable change through a reaction with the analyte or other selected reagent. The distribution of the capture reagent can vary by the concentration or the application (deposition) density of the capture reagent on the transport matrix. The predetermined distribution of the capture reagent on the transport matrix can be achieved through physical or chemical methods as are described below.

The present invention provides an assay which can use specific binding members. A specific binding member or capture reagent, as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies, and antibody fragments, both monoclonal and polyclonal, and complexes thereof, including those formed by recombinant DNA molecules. The term hapten, as used herein, refers to a partial antigen or non-protein binding member which is capable of binding to an antibody, but which is not capable of eliciting antibody formation unless coupled to a carrier protein.

The present invention preferably uses particle detection for a physically detectable change or detectable response in each test zone related to the level of analyte in the sample. Other means for providing a physically detectable change in the test zones are suitable for use in the present invention. For example, and not for limitation, the analyte may be labeled with an indicator to measure electrical conductance or the reflectance or absorption of a characteristic light wavelength. As used herein, the terms signal producing reagent and indicator are meant to include all compounds capable of labeling the analyte or conjugate thereof and generating a detectable response or signal indicative of the level of analyte in the sample.

Analyte, as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. Analyte also includes any antigenic substances, haptens, antibodies, macromolecules, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. In particular, such analytes include, but are not intended to be limited to, ferritin; creatinine kinase MB (CK-MB); digoxin; phenytoin; phenobarbital; carbamazepine; vancoomycin; gentamicin, theophylline; valproic acid; quinidine; luteinizing hormone (LH); follicole stimulating hormone (FSH); estradiol, progesterone; IgE antibodies; vitamin B2 microglobulin; glycated hemoglobin (Gly. Hb); cortisol; digitoxin; N-acetylprocainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B antigen (HBAg); antibodies to hepatitis B antigen (Anti-HB); thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and referenced substances include, but are not intended to be limited to, amphetamine; methamphetamine; barbiturates such as amobarbital, secpbarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone, and opium; phenylcyclidine; and propoxyhene. The details for the preparation of such antibodies and the suitability for use as specific binding members are well known to those skilled in the art.

The sample to be tested can be derived from any biological source, such as a physiological fluid, including whole blood or whole blood components including red blood cells, white blood cells, platelets, serum and plasma; ascites; urine; sweat; milk; synovial fluid; peritoneal fluid; amniotic fluid and other constituents of the body which may contain the analyte of interest. The test sample can be pre-treated prior to use, such as preparing plasma from blood, diluting viscous fluids, or the like; methods of treatment can involve filtration, distillation, concentration, inactivation of interfering compounds, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte. The analyte can be any compound or composition to be detected or measured and which has at least one epitope or binding site.

Generally, the present invention non-diffusively immobilizes a capture reagent on a solid phase support or transport matrix which provides a zone in the path through which the sample flows. The transport matrix can be any solid material to which a capture reagent can be immobilized and includes, but is not intended to be limited to, beads, magnetic particles, paramagnetic particles, microparticles or macroparticles, slides made of glass or other transparent material, capillary and test tubes, fabric or mesh that is woven or cast, and microtiter plates. Such solid phase support can be made from synthetic materials, naturally occurring materials, or naturally occurring materials which have been synthetically modified, and includes, but is not intended to be limited to, cellulose materials, such as paper, cellulose and cellulose derivatives such as cellulose acetate and nirocellulose; fiberglass; naturally occurring cloth such as cotton; synthetic cloth such as nylon; porous gels, such as silica, agarose dextran, and gelatin; porous fibrous matrices; starch based materials, such as cross-linked dextran chains; ceramic materials; olefin or thermoplastic materials including polyvinyl chloride, polyethylene, polyvinyl acetate, polyamide, polycarbonate, polystyrene, coplymers of vinyl acetate and vinyl chloride, combinations of polyvinyl chloride-silica; and the like.

An assay device for the present invention can have many configurations, some of which are specifically illustrated herein. Often these assay devices use a transport matrix which is a porous material or wicking member. By the term porous is meant that the material is one through which the test sample can easily pass and which supports the capture reagent for exposure to the test sample. The transport matrix includes, but is not limited to, both bibulous and non-bibulous solid phase materials. In the present invention, the transport matrix can include a fiberglass, cellulose, or nylon pad for use in a pour and flow-through assay device having multiple layers for multiple assay reagents; a test strip for wicking or thin layer chromatographic capillary action (e.g., nitrocellulose) techniques; or other porous or open pore materials well known to those skilled in the art (e.g., sintered polyethylene sheet material).

Figure 4:
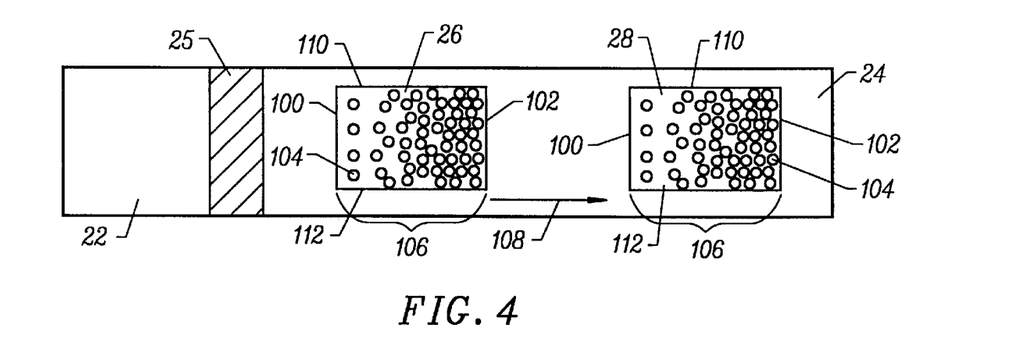
FIG. 4 is an isolated view of a transport matrix having two detection zones utilizing the present invention.

The present invention provides a matrix used to transport the sample across an assay test zone for non-instrumented or instrumented assays to produce qualitative or quantitative results. Referring to FIG. 4, a preferred embodiment of the present invention provides the lateral flow assay strip 22 from FIG. 1 which includes three zones of which two detection zones 26 and 28 are test zones and one of the test zones is a reference zone. A first zone 25 treats the sample with a chemical reagent. The first detection zone 26 produces a signal with intensity inversely proportional to analyte concentration and the second detection zone 28 acts as a reference and produces a signal that is directly proportional to analyte concentration. The sum of the signals from the first and second detection zones 26, 28 is substantially equal at all analyte concentrations. Quantitative or qualitative results are achieved by instrumental reading of color intensity on the first detection zone 26, the second detection zone 28 or both the first and second detection zones 26, 28. The results expressed by any one detection zone can also be determined as a proportion of the sum of the actual results expressed by both detection zones. Quality reference is achieved by instrumental reading of both detection zones, the sum of which should be substantially constant within a specified range.

The embodiment in FIG. 4 provides examples of two preferred configurations including a competitive configuration and an inhibition configuration. The present invention is not limited to these examples and is suitable for use other immunoassays, e.g., sandwich type immunoassays.

Using a competitive type configuration the first zone 25 comprises a bibulous material containing a diffusively immobilized, particle-linked antigen. The first detection zone 26 is separate and distinct from the first zone 25, and is located at some distance toward the distal end 29 of the transport matrix 22. The first detection zone 26 includes a bibulous material containing a non-diffusively immobilized antibody capable of binding the particle-linked antigen and free sample antigen.

The second detection zone 28 is separate and distinct from the first detection zone 26, and is located at some distance toward the distal end 29 of the transport matrix 22 from the first detection zone 26. The second detection zone 28 includes a bibulous material containing a non-diffusively immobilized first member of a specific binding pair, capable of specifically binding to its specific binding partner which is the second member of the specific binding pair on the surface of the particle-linked antigen. This second member of the specific binding pair is not antigenically related to the sample antigen so it will not effectively compete with the antigen to bind to an anti-antigen monoclonal antibody.

The sample is applied to the transport matrix 22 at the application site or first zone 25. The particle-linked antigen is located at or near the application site. The sample containing a sample antigen reconstitutes the dried particle-antigen conjugate by dissolving or dispersing the conjugate, and the mixture of conjugated and free analyte moves via bibulous wicking action to the first detection zone 26, where the free antigen and particle-conjugated antigen compete for non-diffusively immobilized antibody at this zone. That portion (e.g., from 0% to 100%) of the particle-conjugated antigen which binds to the non-diffusively immobilized antibody is retained in the first detection zone 26. The antigen-particle conjugate that does not bind to the first detection zone 26 and migrates to the second detection zone 28, where substantially all of the portion of the particle-conjugated antigen not retained in the first detection zone 26 is bound by the non-diffusively immobilized first member of the specific binding pair in the second detection zone 28.

Using an inhibition type configuration, the first zone 25 includes a bibulous material containing a diffusively immobilized, particle-linked antibody capable of binding sample antigen. The first detection zone 26 is separate and distinct from the first zone 25, and is located some distance toward the distal end 29 of the bibulous strip. The first detection zone 26 includes a bibulous material containing a non-diffusively immobilized antigen capable of being bound by the particle-linked antibody.

The second detection zone 28 is separate and distinct from the first detection zone 26, and is located some distance toward the distal end 29 of the bibulous strip. The second detection zone 28 includes a non-diffusively immobilized first member of a specific binding pair capable of specifically binding to its specific binding partner which is the second member of the specific binding pair on the surface of the particle-linked antigen. This second member of the specific binding pair is not antigenically related to the sample antigen so it will not effectively compete with the antigen to bind to an anti-antigen monoclonal antibody.

The fluid sample is applied to the transport matrix 22 adjacent to the first zone 25 where the particle-linked antibody is located. Sample antigen which may be present in the sample reconstitutes the particle-antibody conjugate and is bound by the conjugate. The bound antigen:antibody-particle complex, as well as unbound antibody-particle complex, are transported or migrate via capillary or wicking action to the first detection zone 26 where substantially all of the free antibody-particle conjugate is bound by the non-diffusively immobilized antigen. The bound sample antigen:antibody-particle complex migrates through the first detection zone 26 to the second detection zone 28, where substantially all of it is bound by the non-diffusively immobilized first member of the specific binding pair.

In the configurations described above, the amount of a physically detectable change present at the first detection zone 26 is an inverse measure of the sample analyte concentration, and the amount of the physically detectable change at the second detection zone 28 is a direct measure of the sample analyte concentration. The physically detectable changes combined from first and second detection zones 26, 28 are approximately constant across the entire range of sample analyte concentration. This total detectable response or signal serves as a reference mechanism for both the assay procedure and reagent quality. Thus, if the total signal is below a specified range, the user is notified of an error. Furthermore, the specific reason for the incorrect assay procedure can be identified. For example, the error can be identified as operation outside the specified temperature and/or humidity range, insufficient sample volume, expired reagents, or the like.

The assay quantification can be determined by reading the first detection zone 26, the second detection zone 28, or both the first and second detection zones 26, 28. The sample concentration output is a result of a calibration algorithm related to the first detection zone 26 alone, the second detection zone 28 alone or both the first and second detection zones 26 and 28 together. This can result in a more reliable quantitative analyte concentration result. The summation of the detectable responses or signal from the first and second detection zones 26 and 28 to produce a substantially constant total signal regardless of analyte concentration provides a reference mechanism for accurate assay performance.

In a preferred embodiment, the transport matrix configuration may be of any dimensions which provide the desired number of zones and which permit (a) the desired binding reactions to be completed in a reproducible manner and (b)

detection of the physically detectable change or the reaction indicator to occur. Preferably, the present transport matrix is a total of no more than about 100 mm in length and about 6 mm wide, and more preferably, from about 10 mm to about 40 mm in length and about 1 mm to about 5 mm wide. The transport matrix is advantageously integrated into any reflectance based instrument, and more preferably, into a disposable electronic assay device, such as that described in above related applications, previously incorporated by reference. Although the chemistry and configurations of the present invention may be used in an integrated assay device, the present invention can be used in any other instrumented reflectance or transmission meter as a replaceable reagent.

The transport matrix can comprise a plurality of zones along its length. The zones can contain diffusively or non-diffusively bound reagents. Each zone can be from about 0.1 mm to about 10 mm wide, more preferably from about 0.25 mm to about 5 mm wide. There will be a minimum of two zones and a maximum of about 10 or more zones, depending on the number of assays to be conducted on one transport matrix.

The transport matrix can be one continuous section of bibulous material or can be composed of one, two, three or more sections. Each zone may be a separate bibulous material where each zone is in fluid communication with adjacent zones, or two or more adjacent zones may share a common material, with the other zones being different materials. The transport matrix including each of the zones can be composed of the same or different bibulous materials. The bibulous material permits fluid communication between the various zones, spacers (if present) and sample application site by wicking or capillary action upon application of a fluid sample.

In the preferred embodiments, the transport matrix includes a bibulous substrate to which the capture reagent, which may be labeled, are diffusively or non-diffusively immobilized. Non-diffusive immobilization can be conducted by adsorbing, absorbing, crosslinking or covalently attaching the capture reagent to the bibulous substrate.

Diffusive immobilization can be conducted by formulating the assay reagent(s) to be immobilized (e.g., by dissolving in a suitable solvent such as water, a $C_1$–$C_4$ alcohol or mixture thereof, along with any desired additives), applying the resulting formulation to the bibulous material of the membrane, filter or transport layer in the desired location(s), and drying the material. Suitable additives may include detergents, proteins, blocking agents, polymers, sugars or the like. Alternatively, the additive(s) and assay reagent(s) may be applied to the membrane, filter or transport layer by precoating with a "blocking agent", water soluble polymer, sugar or detergent, followed by depositing the conjugate or conjugate formulation and drying the material. Diffusive immobilization allows rapid reconstitution and movement of reagents, whether reacted or unreacted, through the bibulous substrate. Non-diffusive immobilization can be accomplished by covalently attaching, adsorbing or absorbing the capture reagent to the transport matrix.

The zones can contain reagents diffusively or non-diffusively bound including, but not limited to, antibodies, antigens, enzymes, substrates, small molecules, proteins, recombinant proteins, viral or bacterial lysate, receptors, sugars, carbohydrates, polymers like PVA and detergents.

Referring to the preferred embodiment of the transport matrix 22 shown in FIG. 4, the first and second detection zones 26, 28 have a leading boundary 100 and a trailing boundary 102. Within each detection zone 26, 28 is a predetermined distribution of deposits as dots 104 of a capture reagent in a pattern 106. The printed pattern 106 increases the density of the dots 104 across each detection zone 26, 28 from the leading boundary 100 to the trailing boundary 102 in the direction of sample flow indicated by arrow 108. Preferably, the density of the dots 104 from one side 110 of each detection zone to the other side 112 is approximately uniform. The capture efficiency of the pattern 106 illustrated in FIG. 4 effectively increases at a approximately constant rate across each detection zone 26, 28 to present a uniform gradient.

The dots 104 in the pattern 106 are mechanically or physically applied to the transport matrix 22 using a conventional inkjet printer. Other applicators suitable for use with the present invention include, but are not limited to, a fountain pen, a pad printer, pipette, air brush, metered dispensing pump and tip system, or the like. Other applicators which accurately measure the reagents onto appropriate zones of the predetermined distribution are also suitable. The dots 104 can be any shape or size and can vary in these dimensions within the pattern 106.

Figure 5:
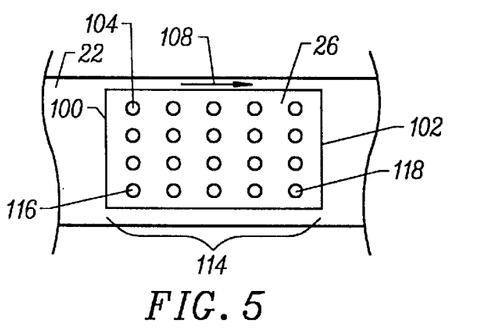
FIG. 5 is an isolated view of a detection zone utilizing a uniform distribution of dots of a capture reagent in the present invention.

Another embodiment of the present invention is to physically apply the predetermined distribution of dots 104 of the capture reagent within the detection zone 26 in a uniform pattern 114 as illustrated in FIG. 5. The printed uniform pattern 114 increases the concentration of the capture reagent within each dot 104 across the detection zone 26 from the leading boundary 100 to the trailing boundary 102 in the direction of sample flow as indicated by the arrow 108. As a result, individual dot 116 has a lower concentration of capture reagent than dot 118.

Figure 6:
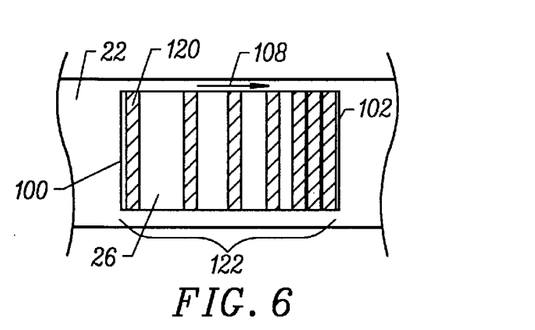
FIG. 6 is an isolated view of a detection zone utilizing a increasing frequency of stripes of a capture reagent in the present invention.

Another preferred embodiment illustrated in FIG. 6 applies deposits of the capture reagent to the transport matrix 22 in a series of stripes 120 across the detection zone 26 from the leading boundary 100 to the trailing boundary 102 in the direction of sample flow 108 to form a pattern 122 having a predetermined distribution. Preferably, the stripes 120 extend across the width of the detection zone which is perpendicular to the direction of sample flow. The series of stripes 120 vary in frequency across the detection zone 26. In this embodiment, the concentration of the capture reagent in each of the stripes 120 is the about equal. The capture efficiency of the pattern 122 increases due to the increasing frequency of the stripes 120. The capture efficiency of the pattern illustrated in FIG. 6 effectively increases at an approximately constant rate across the detection zone 26 to present a uniform gradient.

The stripes 120 in the pattern 122 are mechanically or physically applied to the transport matrix 22 using a printer, air brush, metered dispensing pump and tip system, pipette, or the like. The stripes 120 can be any width and can vary in width within the pattern 122. Alternately, the chemical content or concentration of the capture reagent in each of the stripes 120 may vary along the pattern 122.

Figure 7:
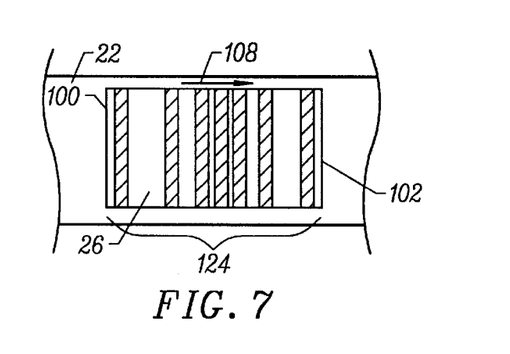
FIG. 7 is an isolated view of a detection zone utilizing non-uniform distribution of stripes of a capture reagent in the present invention.

Another embodiment of the present invention which provides the combination of varying the frequency of the series of stripes 120 as well as their concentration to form a pattern 124 having a predetermined distribution is illustrated in FIG. 7. The capture efficiency of the pattern 124 effectively increases from the leading boundary 100 towards the middle of the detection zone 26 and then effectively decreases toward the trailing boundary 102 demonstrating the variety of the present invention in disclosing a non-uniform gradient.

Figure 8:
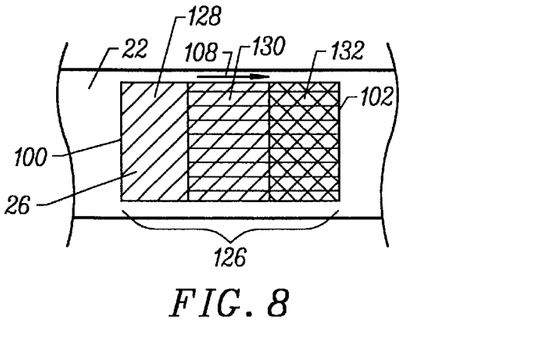
FIG. 8 is an isolated view of a detection zone utilizing overlapping stripes of capture reagent in the present invention.

The embodiment illustrated in FIG. 8 provides a predetermined distribution of increasing concentration and/or density of the capture reagent to form a pattern 126 from the leading boundary 100 to the trailing boundary 102 across the detection zone 26. A first stripe 128 substantially covers the detection zone 26. A second stripe 130 partially overlaps the first stripe 128, but leaves an area where only the first stripe 128 is present. In a similar fashion, another stripe 132 partially overlaps the first and second stripes 128, 130, but leaves an area where only the first stripe 128, and where only the first and second stripes 128, 130 are present. As a result, the pattern 126 formed is a cascade of overlapping stripes. The concentration of the capture reagent increases in the area where the stripes successively overlap. If the concentration of capture reagent is the same in each stripe 128, 130, 132, then the areas of overlap doubles and triples the capture reagent concentration. Varying the amount of capture reagent in each stripe is also suitable.

Examples of patterns applied to the transport matrix are illustrated in FIGS. 4–8, but it is to be understood that the present invention is not limited to the particular shapes of the deposits illustrated such as the dots and stripes nor the specific frequency or size of the designs.

One of the present invention's preferred chemical methods of applying the capture reagent include using a conventional printer to print a pattern representing a predetermined distribution of the capture reagent onto the transport matrix. The printed pattern is then treated to modify the effectiveness of the capture reagent in a predetermined distribution by adjusting the efficiency of the capture reagent to effectively bind with the analyte or its conjugate. For example and not for limitation, the capture efficiency of the capture reagent can be adjusted by using a blocking reagent which binds with the capture reagent or with the analyte to effectively decrease the ability of the capture reagent to bind with the analyte or its conjugate.

Figure 9:
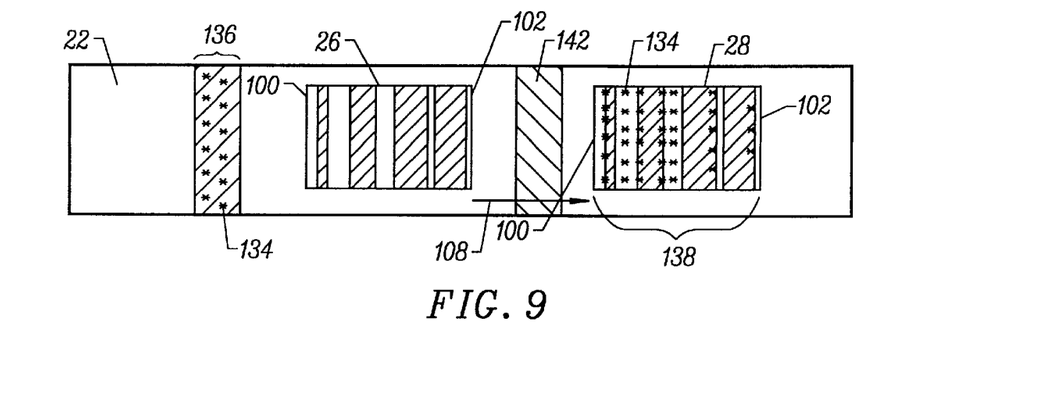
FIG. 9 is an isolated view of a transport matrix having two detection zones utilizing the present invention.

Two configurations of a preferred embodiment which chemically adjusts the capture reagent efficiency are illustrated in FIG. 9, One configuration is to apply a blocking reagent 134 in a zone 136 prior to the detection zone 26 along the direction of sample flow as indicated by arrow 108. The zone 136 containing the blocking reagent can be separate from the detection zone 26 or overlap the leading boundary 100. The blocking reagent 134 is then distributed as the sample flows across the detection zone 26. Alternately, the blocking reagent 134 can be distributed across the detection zone 26 prior to application of the sample to the transport matrix. A solution which is capable of diffusing the blocking reagent 134 can be used to treat the transport matrix 22 prior to exposure with the sample such as during manufacture of the transport matrix 22.

A second configuration of a preferred embodiment which chemically adjusts the capture reagent efficiency is to apply the blocking reagent 134 as a second pattern of predetermined distribution over the pattern 138 of capture reagent. The predetermined distribution of the capture reagent represented by pattern 138 is a uniform series of stripes 140. The second pattern of the blocking reagent 134 is a predetermined distribution which decreases in concentration and/or density of the blocking reagent 138 from the leading boundary 100 to the trailing boundary 102 of second detection zone 28. The type of blocking reagent 134 is selected to bind with either the analyte or the capture reagent to decrease the effectiveness of the capture reagent to bind with the analyte. As specifically illustrated, a gradient of increasing capture efficiency from the leading boundary 100 to the trailing boundary 102 is formed by the interaction of the blocking reagent 134 and either the capture reagent or the analyte.

Blocking reagents can be either specific or non specific in their blocking effect on the capture reagent or analyte. Examples of non-specific blocking reagents include polymers and particles. Specific blocking reagents include antibodies and antibody conjugates with polymers or particles wherein the larger size of the particle slows its rate of diffusion. Other specific blocking reagents include antigens and antigen conjugates with polymers or particles of varying size.

Bulking materials can be used as another method of varying the concentration of the capture reagent, and thus modifying the capture efficiency of the detection zone, in a predetermined distribution. The bulking material can be combined with the capture reagent as part of the original mix prior to depositing the capture reagent onto the transport matrix. Where the bulking material is deposited onto the transport matrix with the capture reagent it acts as a non-specific blocking reagent to the capture reagent.

Figure 10:
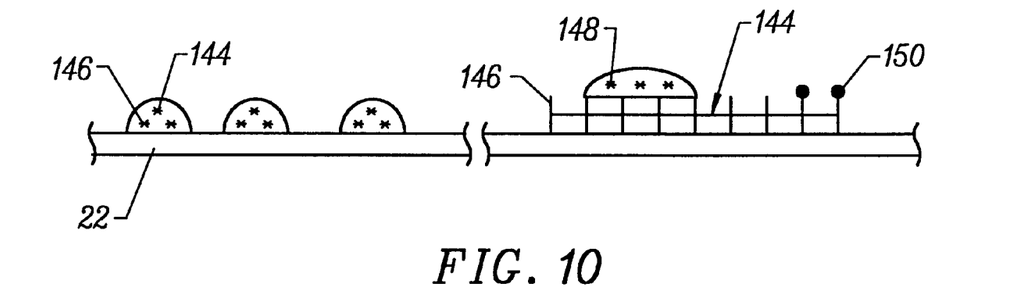
FIG. 10 is cross-sectional side view of a transport matrix with bulking materials and capture reagents of the present invention deposited thereon.

As illustrated in FIG. 10, a simplified representation demonstrates a bulking material 144 mixed with a capture reagent 146 prior to deposition on a transport matrix 22. Also illustrated is a bulking material 148 used as a non-specific blocking reagent on the binding sites of the capture reagent 146 compared to a specific blocking reagent 150 on a binding site of an individual capture reagent.

Another method of modifying the capture efficiency of the detection zone to create a predetermined distribution of the physically detectable change, is also illustrated by FIG. 9. In this embodiment, the detection zone 28 can be coated or impregnated with a diffusion control material which modifies the flow 108 of the sample across the detection zone 28. When the diffusion rate of the sample across the detection zone 28 is adjusted, the capture efficiency of the capture reagent will be correspondingly adjusted because there will be more or less time for the binding with the capture reagent to occur. For example and not limitation, a suitable diffusion control material for use with the present invention is dextran. Other suitable diffusion control materials include, but are not limited to, polyethylene glycol and other polymeric materials soluble in the sample matrix.

For certain types of assays such as OSTEOMARK® NTx (Ostex International), a blocking reagent which competitively binds with the capture reagent can be added to zone 128 prior to the detection zone 26. The competitive blocking reagent will diffuse with the sample and tend to reduce the capture efficiency. As the competitive blocking reagent diffuses across the detection zone 26, its concentration will decrease and the capture efficiency of the capture reagent will increase creating a reverse gradient. The embodiment of this method is suitable for use with other assays and suitable competitive blocking reagents include, but are not limited to, salts such as sodium chloride, urea, and chaotropes.

An analyte such as OSTEOMARK® NTx can be desensitized by adding a synthetic peptide analog or other analyte to the transport matrix 22 prior to the detection zone 26. This will reduce the capture efficiency at the leading boundary of the detection zone. The capture efficiency then increases as the analyte encounters less competition from the peptide analog and becomes more sensitive to binding with the capture reagent. At low concentrations of analyte, the initial sensitivity is poor at the low end of the calibration curve for the chemical reactions of the particular assay. Adding a small, predetermined amount of analyte to diffuse along the transport matrix prior to or simultaneously with the sample, adjusts the sensitivity of the assay further along the calibration curve into a more sensitive portion of the calibration curve.

The present invention also provides a method of minimizing the deleterious impact of high analyte concentrations on producing a "hook effect" in the embodiment utilizing the sum of measuring the physically detectable change across two or more zones. Referring again to FIG. 9, a trapping zone or stripe 142 is optionally added to the transport matrix 22. The trapping zone 142 includes a trapping reagent immobilized therein which binds excess analyte beyond the capture capacity of the first detection zone 26. The trapping reagent binds to latex which would otherwise bind in the second detection zone 28 and provides an inaccurate sum of measuring the physically detectable changes in the first and second detection zones 26 and 28. Using this embodiment of the present invention will identify the sum of the measurements below a predetermined minimum as the result of an analyte concentration above the range the device was intended to measure.

Figure 11:
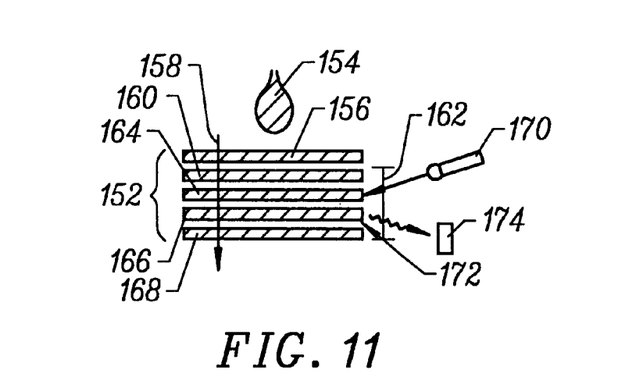
FIG. 11 is a side view of a stack configuration for a transport matrix and reflectometer using the present invention.

Another embodiment of the present invention using a different configuration than the previous examples for the transport matrix is illustrated by the exploded view in FIG. 11. A transport matrix 152 is arranged in a layered, stack configuration. A sample 154 to be analyzed for one or more selected analytes is applied to a first layer 156 of bibulous material which can be untreated or may contain a reagent for treating the sample as done by the first zone 25 in FIG. 4. The sample 154 then flows in the direction of arrow 158 to layer 160 which is the leading boundary of a detection zone 162. The layer 160 contains the capture reagent non-diffusively immobilized therein. Similarly, layers 164, 166, and 168 each separately contain increasingly larger amounts of the capture reagent non-diffusively immobilized therein. Thus, the concentration and/or the density of the capture reagent increases across the detection zone 162 from layer 160 to layer 168. In operation, the sample laterally wicks across the detection zone 162 from layer 160 to layer 168. The sides 172 of the layers 160, 164, 166, and 168 are illuminated by a light source 170 from a conventional reflectometer and diffusely reflects optical radiation to a detector 174. More detection zones can be added to the transport matrix 152 by increasing the number of layers of bibulous material.

Figure 12:
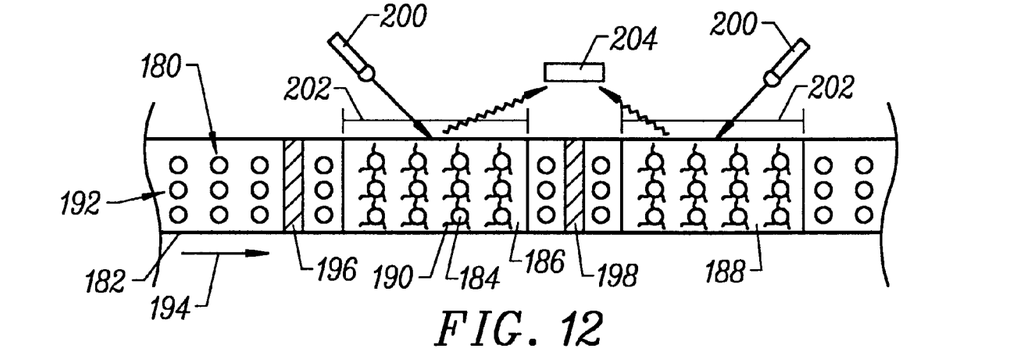
FIG. 12 is a cross-sectional view of a capillary tube enclosing a transport matrix of the present invention.

Another embodiment of the present invention using a different configuration than the previous examples for the transport matrix is illustrated by FIG. 12. A transport matrix 180 is contained within an enclosure 182 such as a capillary tube. The transport matrix 180 includes a solid phase support 184 packed within the enclosure. Within a first detection zone 186 and a second detection zone 188, the solid phase support 184 has a capture reagent 190 immobilized thereon. The sample is introduced to the enclosure 182 through an inlet port 192 and flows or wicks across the enclosure 182 in the direction of arrow 194. The physically detectable changes in detection zones 186 and 188 are illuminated by light sources 200 through transparent sections 202 in the wall of the enclosure. The diffusely reflected optical radiation is measured by a detector 204.

In one configuration of FIG. 12, the amount of capture reagent 190 is uniformly distributed across the detection zones 186 and 188. The enclosure 182 includes zones 196 and 198 containing a blocking reagent which form a predetermined distribution of the capture reagent efficiency when transported across the respective detection zones 186 and 188 preceding the flow of the sample.

In an alternate configuration illustrated by FIG. 12, the capture reagent 190 is packed into the enclosure 182 to immediately form the desired predetermined distribution by varying the amount of capture reagent across each detection zone 186, 188. As a result, zones 196 and 198 are not needed.

The transport matrices shown and described herein can be configured by several assembly methods. Conventional methods of immobilizing a reagent, by dipping a transport matrix in a solution containing the reagent and subsequently drying are suitable for use in portions of the present invention. In such a hybrid method, an approximately uniform layer or coating of a reagent is first deposited on the transport matrix. The uniform deposit is then modified by deposited a pattern of a second reagent over the first reagent or in a zone on the transport matrix prior to the first reagent. This method can be used with capture reagents and diffusion control reagents as the first reagents. Blocking reagents can be used as the second reagent. The following examples specify the details of these methods.

Having generally described the present invention, a further understanding can be obtained by reference to the following specific examples, which are provided herein for purposes of illustration only and are not intended to be limiting of the present invention.

EXAMPLE 1

The following strip assembly and capture reagent immobilization methods were used in the construction of the inventive examples. Assay strips for the examples were prepared by laminating a transport matrix to a plastic backing by joining bibulous material to a sheet of polyvinyl acetate (0.01" thick) using a double-stick adhesive or a transfer adhesive.

A card of polyvinyl acetate sheet (0.01" thick) was cut to about 2.3 cm by 10 cm. The size of the card varied, depending on the desired assay card size. The polyvinyl acetate backing was marked with pencil lines along the length at appropriate positions indicating the location of the various assay strip zones. Double stick adhesive, such as 3M 465 was applied to the polyvinyl acetate, so as to cover the surface with the pencil lines, and firm pressure was applied with a roller assembly making sure to eliminate the formation of bubbles. The release liner of the double-stick adhesive was removed and the transport matrix or paper assay sections applied to the correct location, guided by the pencil lines, and firm pressure was applied with a roller assembly making sure to eliminate bubbles. Care was taken to ensure that each section of the bibulous assay matrix was in fluid communication with its neighbor. Finally, individual assay strips were cut, each 0.3 cm wide along the length of the card, resulting in assay strips 2.3 cm long by 0.3 cm wide. This was accomplished using a die cutter or a standard paper cutter.

For the blocking reagents identified in Table 1, the blocking reagent was covalently coupled to latex microparticles having a preferred size range of about 0.1 $\mu$m to about 20 $\mu$m and these particles were drawn into the transport matrix by capillary action. The microparticle method was accomplished by first covalently immobilizing the desired blocking reagent to microspheres with carboxyl functional groups as follows: To a suspension of 0.4 $\mu$m microspheres-COOH (e.g., Bangs Laboratories) 1.1 molar equivalents (relative to the COOH groups on the bead surface) of 1-ethyl-3-(dimethylaminopropyl)carbodiimide (EDAC, Sigma E 0388) and 1.1 molar equivalents of N-hydroxysuccimimide (NHS, Pierce 24500) in 50 mM 2-(N-morpholino) ethanesulfonic acid buffer (MES, Sigma M-5287), pH 6, were added at room temperature with stirring for 30 minutes. Then the suspension was centrifuged and washed in MES to remove excess NHS and EDAC. Subsequently, the desired blocking reagent was added with 50 mM sodium borate, pH 8.5, (the protein is at a 10 fold molar excess over the COOH functional groups on the bead surface), allowed to react for 2 hours at room temperature, and then purified by centrifuging, followed by washing and recentrifugation. The microparticles then had the desired blocking reagent covalently immobilized. The blocking reagent-particle suspension was mixed, a 2–10 μL sample picked up using a pipette, and immediately placed it on the transport matrix prior to the capture reagent.

To prepare the antigen conjugate for the capture reagent, mouse IgG or bovine IgG (BgG (Bovin Gamma-Globulin)) was activated with 0.15M NaCl in 50 mM phosphate (PBS) at pH 7.2 with succinimidyl-4-(N-maleimidomethyl) Cyclohexane-1-Carboxylate (SMCC, Pierce #22320) in a 50:1 mole ratio by reacting for about 60 minutes at room temperature. The maleimidated IgG was passed down a Sephadex G15 (10 ml) column equilibrated with 50 mM sodium phosphate and 1 mM EDTA, pH 7.0. C-peptide (a synthetic antigen obtained from Ostex International) was added dropwise to the maleimidated IgG, in 50 mM sodium phospate and 1 mM EDTA, pH 7.0, in a 50:1 mole ratio (c-peptide: IgG) and allowed to react for about 2 hours at room temperature. Subsequently, the mixture was passed down a Sephadex G25 column equilibrated with PBS, pH 7.2, to remove unreacted synthetic antigen. The ratio of c-peptide:IgG was varied to yield the materials listed in Table 1.

For treatment of the transport matrix with anti-NTx (Mab 1H11), BSA, or BgG (Bovine Gamma-Globulin), a single stripe having a width of about 1.5 mm was deposited across the detection zone using the striper BIOLINE® Programmable Dispensing System made by ISMECA Group of Carlsbad, Calif., fitted with two Digipense 2000 pumps made by IVEK Corporation of North Springfield, Vt. For the treatment with C-IgG the two ratios listed in Table 1 were deposited as two separate stripes, each having a width of about 0.75 mm across the detection zone using the same striper. The reflectance density was measured at the leading boundary (L) and trailing boundary (T) of the detection zone (zone).

TABLE 1

| Treatment | NTx (nM) | Reflectance Leading(L) | Density Trailing(T) | L/T ratio | Zone Width(mm) |
|---|---|---|---|---|---|
| Control | 30 | 0.69 | 0.41 | 1.68 | 1.3 |
| | 300 | 0.61 | 0.49 | 1.24 | 1.5 |
| | 1000 | 0.43 | 0.36 | 1.19 | 1.5 |
| Anti-NTx | 30 | 0.71 | 0.68 | 1.04 | 1.4 |
| Ab (1H11) | 300 | 0.57 | 0.56 | 1.01 | 1.4 |
| 25 ug/mL | 1000 | 0.43 | 0.41 | 1.05 | 1.4 |
| 1% BSA- | 30 | 0.60 | 0.52 | 1.15 | 1.5 |
| 0.403 um | 300 | 0.44 | 0.38 | 1.15 | 1.4 |
| white particles | 1000 | 0.37 | 0.34 | 1.08 | 1.5 |
| 1% BgG- | 30 | 0.61 | 0.58 | 1.05 | 1.5 |
| 0.403 um | 300 | 0.45 | 0.39 | 1.15 | 1.5 |
| white particles | 1000 | 0.39 | 0.38 | 1.08 | 1.3 |
| 1% 1H11- | 30 | 0.60 | 0.51 | 1.17 | 1.5 |
| 0.403 um | 300 | 0.53 | 0.51 | 1.03 | 1.4 |
| white particles | 1000 | 0.39 | 0.38 | 1.03 | 1.6 |
| Gradient Zones: | 30 | 0.60 | 0.58 | 1.03 | 1.9 |
| CIgG(5:1): | 300 | 0.51 | 0.47 | 1.08 | 1.9 |
| CIgG(50:1) | 1000 | 0.37 | 0.32 | 1.15 | 1.9 |
| Gradient Zones | 30 | 0.65 | 0.55 | 1.18 | 1.8 |
| | 300 | 0.51 | 0.46 | 1.10 | 2.0 |
| CIgG(10:1): CIgG(50:1) | 1000 | 0.39 | 0.39 | 1.00 | 2.0 |

The reflectance densities presented in Table 1 were measured with a hand-held reflectance densitometer made by Gretag which uses about a one mm diameter measurement area. Besides a control, six different capture reagent distributions were used with three different concentrations of OSTEOMARK® NTx as an analyte to demonstrate the present invention's ability to provide a more uniform distribution of the physically detectable change across the detection zone. As demonstrated by the reflectance densities measured at the leading and trailing boundaries of the detection zones, their ratios significantly decreased indicating a more uniform distribution of the physically detectable change.

EXAMPLE 2

The same strip assembly method used in Example 1 were followed to form a control and three different combinations of gradient lines. A non-diffusive immobilization was accomplished using the ink jet printer Series 810 Dispensing System made by Synergy Research of West Lebanon, N.H., using CorelDraw software, to accurately measure the various capture reagents and their concentrations listed in Table 2 onto appropriate detection zones of the transport matrix. In this case, the capture reagent solution was diluted to between 0.01 mg/mL and 10 mg/nL with 0.15M NaCl in 50 mM phosphate (PBS), pH 7.2, and introduced into the application device. The application device was then positioned above the appropriate detection zone and the immobilization material was printed as either a single stripe or as a series of discrete stripes having a increasing frequency of dot distribution across the detection zone. The width of the discrete stripes was about 0.25 mm to about 5 mm and preferably about 0.5 to about 1.5 mm. The transport matrix was then dried at 45° C. for 10 minutes or until dry. The transport matrix was washed and preserved with 1% polyvinyl pyrrolidine and then dried again.

Table 2 presents the results of the reflectance density measurements for each pattern of dot matrix gradient at three different concentrations of OSTEOMARK® NTx, at the leading and trailing boundaries of the detection zones. The first two gradient patterns in Table 2 were produced by the printer depositing a continuous gradient of dot density. The final treatment was a discontinuous gradient of dot density consisting of four separate stripes. Table 2 also illustrates the effect of slight differences in the steepness of the gradient, e.g., 0% to 100% versus 20% to 100% dot density.

TABLE 2

| Treatment | NTx (nM) | Reflectance Leading(L) | Density Trailing(T) | L/T ratio | Zone Width(mm) |
|---|---|---|---|---|---|
| Control | 30 | 0.52 | 0.30 | 1.73 | 3.0 |
| Solid Line | 300 | 0.43 | 0.28 | 1.53 | 3.0 |
| | 1000 | 0.30 | 0.19 | 1.57 | 3.0 |
| | 3000 | 0.23 | 0.21 | 1.09 | 3.0 |
| Gradient | 30 | 0.46 | 0.36 | 1.27 | 2.8 |
| line: | 300 | 0.39 | 0.30 | 1.30 | 2.8 |
| 0–100% | 1000 | 0.24 | 0.22 | 1.09 | 2.8 |
| | 3000 | 0.17 | 0.17 | 1.00 | 2.8 |
| Gradient | 30 | 0.67 | 0.65 | 1.03 | 3.0 |
| line: | 300 | 0.52 | 0.52 | 1.00 | 3.0 |
| 20–100% | 1000 | 0.35 | 0.34 | 1.03 | 3.0 |
| | 3000 | 0.26 | 0.26 | 1.00 | 3.0 |
| Gradient | 30 | 0.66 | 0.57 | 1.15 | 2.8 |
| line: | 300 | 0.55 | 0.51 | 1.08 | 2.8 |
| 4 lines of | 1000 | 0.34 | 0.32 | 1.06 | 2.8 |
| 20, 40, 80, & 100% | 3000 | 0.23 | 0.23 | 1.00 | 2.8 |

The reflectance densities presented in Table 2 demonstrate the present invention's ability to provide a more uniform distribution of the physically detectable change across the detection zone. As demonstrated by the reflectance densities measured at the leading and trailing boundaries of the detection zones, their ratios significantly decreased indicating a more uniform distribution of the physically detectable change.

Numerous modifications and variations of the present invention are possible in light of the above teachings. It is therefore to be understood that within the scope of the appended claims, the invention may be practiced otherwise than as specifically described herein.

What is claimed is:

1. A transport matrix producing a physically detectable change in a predetermined distribution across a detection zone which correlates with the amount of selected analyte in a sample, the matrix comprising;
   a detection zone having a capture reagent yielding a physically detectable change which correlates with the amount of selected analyte in the sample, the detection zone being defined by an area in which the physical detectable change is sampled, the detection zone having a leading boundary which first encounters the sample and a trailing boundary which encounters the sample after being transported across the detection zone, the capture reagent being immobilized on the matrix in a varied, predetermined distribution from the leading boundary to the trailing boundary of the detection zone so that the physical detectable change has a substantially uniform distribution in the direction of the sample flow, the predetermined distribution of immobilized capture region being a plurality of deposits of the capture reagent, the density of the plurality of deposits increasing from the leading boundary to the trailing boundary of the detection zone.

2. The matrix of claim 1 wherein the predetermined distribution of immobilized capture reagent increases the concentration of the capture reagent from the leading boundary to the trailing boundary of the detection zone.

3. The matrix of claim 1 wherein the predetermined distribution of immobilized capture reagent increases the application density of the capture reagent from the leading boundary to the trailing boundary of the detection zone.

4. The matrix of claim 1 wherein the predetermined distribution of immobilized capture reagent is a plurality of stripes of the capture reagent, the plurality of stripes extending across the width of the detection zone perpendicular to the transportation of the sample.

5. The matrix of claim 4 wherein the frequency of stripes within the plurality of stripes increases from the leading boundary to the trailing boundary of the detection zone.

6. The matrix of claim 4 wherein each stripe of the plurality of stripes successively increases the concentration of capture reagent within the stripe from the leading boundary to the trailing boundary.

7. The matrix of claim 4 wherein the plurality of stripes overlap one another to form a cascade of areas successively increasing the concentration of capture reagent from the leading boundary to the trailing boundary.

8. The matrix of claim 1 wherein the detection zone further includes a bulking reagent and the capture reagent includes a conjugate which increases in distribution relative to the bulking reagent from the leading boundary to the trailing boundary of the detection zone.

9. The matrix of claim 1 wherein the detection zone further includes a blocking reagent which reacts with the capture reagent to prevent at least a portion of the capture reagent from reacting further and forms a non-uniform, predetermined distribution of capture efficiency across the detection zone.

10. A transport matrix for determining the presence of selected analyte in a sample, the matrix comprising:
    a detection zone having a capture reagent yielding a physically detectable change which correlates with the amount of selected analyte in the sample, the detection zone having a leading boundary which first encounters the sample and a trailing boundary which encounters the sample after being transported across the detection zone, the physically detectable change being immobilized in a varied, uniform distribution across the detection zone so that the physical detectable change sampled in each area of the detection zone is substantially uniform, the distribution of immobilized capture reagent being a plurality of deposits of the capture reagent, the density of the plurality of deposits increasing from the leading boundary to the trailing boundary of the detection zone.

11. A transport matrix producing a physically detectable change with a signal producing conjugate in a predetermined distribution across a detection zone which correlates with the amount of selected analyte in a sample, the matrix comprising:
    a detection zone having a capture reagent yielding a physically detectable change which correlates with the amount of selected analyte in the sample, the detection zone having a leading boundary which first encounters the sample and a trailing boundary which encounters the sample after being transported across the detection zone, the capture reagent being immobilized in a varied, predetermined distribution from the lead boundary to the trailing boundary of the detection zone so that the physical detectable change has a substantially uniform distribution in the direction of sample flow, the predetermined distribution of immobilized capture reagent being a plurality of deposits of the capture reagent, the density of the plurality of deposits increasing from the leading boundary to the trailing boundary of the detection zone;
    a zone located prior to the leading edge of the detention zone, the zone having a blocking reagent diffusively immobilized therein, the blocking reagent capable of diffusing across the detection zone and modifying the capture efficiency of the approximately uniform distribution of the capture reagent to form non-uniform capture efficiency across the detection zone.

12. The matrix of claim 11 wherein the blocking reagent is selected from the group consisting of an antibody to antigen or carrier molecule or an antibody conjugate with a macromolecule, latex or other microparticle.

13. The matrix of claim 11 wherein the blocking reagent is an analyte complex with a second antibody.

14. The matrix of claim 11 wherein the blocking agent is a salt or an antigen.

15. The matrix of claim 11 wherein blocking reagent reduces the capture reagent from reacting with the analyte or signal producing conjugate, the blocking reagent diffusively transported across the detection zone and consequently decreasing the concentration of the blocking reagent above which the capture reagent can react to a greater extent with the analyte or signal producing conjugate.

16. The matrix of claim 11 wherein the blocking reagent reacts with the capture reagent to prevent at least a portion of the capture reagent from reacting further with the analyte or a signal producing conjugate.

17. The matrix of claim 11 wherein the blocking reagent reacts with the analyte or signal producing conjugate to prevent at least a portion of the analyte or signal producing conjugate from reacting further with the capture reagent.

18. The matrix of claim 11 wherein the matrix further includes a zone located prior to the leading boundary of the detection zone, the zone having the blocking reagent diffusively immobilized therein, the blocking reagent is diffused by the transported sample across the detection zone.

19. A transport matrix producing a physically detectable change in a predetermined distribution across a detection zone which correlates with the amount of selected analyte in a sample, the matrix comprising:
   a detection zone having a capture reagent yielding a physically detectable change which correlates with the amount of selected analyte in the sample, the detection zone having a leading boundary which first encounters the sample and a trailing boundary which encounters the sample after being transported across the detection zone, the capture reagent being immobilized in a varied, predetermined distribution from the leading boundary to the trailing boundary of the detection zone so that the physical detectable change has a substantially uniform distribution in the direction of sample flow, the predetermined distribution immobilized capture reagent being a plurality of deposits of the capture reagent, the density of the plurality of deposits increasing from the leading boundary to the trailing boundary of the detection zone;
   a diffusion control material being distributed within the detection zone, the diffusion control material being slowing the transportation of the sample across the detection zone and increasing capture efficiency of the capture reagent from the leading edge to the trailing edge.

20. The matrix of claim 19 wherein the diffusion control material is selected from the group consisting of dextran, polyethylene glycol, and a polymeric material soluble in the sample.

21. A transport matrix producing a physically detectable change in predetermined distribution across a plurality of detection zones which correlates with the amount of selected analyte in a sample, the matrix comprising:
   first and a second detection zone, each detection zone having a non-diffusively immobilized capture reagent yielding a physically detectable change which correlates with the amount of selected analyte in the sample, each detection zone having a leading boundary which first encounters the sample and a trailing boundary which encounters the sample after being transported across each detection zone, the capture reagent of each detection zone being immobilized in a predetermined distribution from the leading boundary to the trailing boundary of each detection zone, the predetermined distribution of immobilized capture reagent being a plurality of deposits of the capture reagent, the density of the plurality of deposits increasing from the leading boundary to the trailing boundary of each detection zone.

22. The matrix of claim 21 wherein the matrix further includes a trap reagent non-diffusively immobilized on the transport matrix between the first and second detection zones, the trap reagent present in an amount effective to immobilize analyte in excess of the capture capacity of the first detection zone.

23. The matrix of claim 21 wherein the predetermined distribution of capture reagent in each detection zone is the same.

24. A diagnostic device for determining the presence of a selected analyte in a sample with a means for measuring the analyte's presence, the device comprising:
   a housing having an exterior surface and sealing an interior area;
   a receptor configured to receive the sample containing an analyte selected for determining its presence, the receptor located on the exterior surface of the housing;
   at least one transport matrix for reacting the sample with a capture reagent to yield a physically detectable change in a detection zone which correlates with the amount of selected analyte in the sample, the detection zone having a leading boundary which first encounters the sample and a trailing boundary which encounters the sample after being transported across the detection zone, the capture reagent being immobilized in the predetermined distribution from the leading boundary to the trailing boundary of the detection zone so that the physical detectable change has a substantially uniform distribution as it appears to the measurement means, the predetermined distribution of immobilized capture reagent being a plurality of the deposits of the capture reagent, the density of the plurality of deposits increasing from the leading boundary to the trailing boundary of the detection zone.

25. The device of claim 24 wherein the predetermined distribution of immobilized capture reagent increases the concentration of the capture reagent from the leading boundary to the trailing boundary of the detection zone.

26. The device of claim 24 wherein the predetermined distribution of immobilized capture reagent increases the application density of the capture reagent from the leading boundary to the trailing boundary of the detection zone.

27. The device of claim 24 wherein the detection zone further includes a blocking reagent which reacts with the capture reagent to prevent at least a portion of the capture reagent from reacting further and forms a non-uniform predetermined distribution of capture efficiency across the detection zone.

28. The device of claim 24 wherein the matrix includes a second detection zone positioned after the detection zone along the direction of sample flow, the second detection zone having a non-diffusively immobilized capture reagent yielding a physically detectable change which correlates with the amount of selected analyte in the sample, the second detection zone having a leading boundary which first encounters the sample and a trailing boundary which encounters the sample after being transported across each detection zone, the capture reagent immobilized in a predetermined distribution from the leading boundary to the trailing boundary of the second detection zone.

29. The device of claim 28 wherein the matrix further includes a trap reagent non-diffusively immobilized on the transport matrix between the detection zones, the trap reagent present in an amount effective to immobilize analyte in excess of the capture capacity of the first detection zone.

30. A method for determining the level of a selected analyte in a sample, the method comprising the steps of:
   applying and directing the sample to flow across a detection zone on a transport matrix, the detection zone having a leading boundary which first encounters the sample and a trailing boundary which encounters the sample after being transported across the detection zone; and
   distributing a physically detectable change in a predetermined pattern in the direction of sample flow across a detection zone on the transport matrix which correlates with the amount of selected analyte by immobilizing a plurality of capture reagent in a predetermined distribution within the detection zone, the density of the plurality of deposits increasing from the leading boundary to the trailing boundary of the detection zone.

31. The method of claim 30 wherein the distributing step includes distributing the physically detectable change uniformly across the detection zone.

32. The method of claim 30 wherein the immobilizing step includes depositing the capture reagent in a predetermined pattern increasing the application density of the capture reagent from a leading boundary to the trailing boundary of the detection zone.

33. The method of claim 30 wherein the immobilizing step includes depositing the capture reagent in a predetermined pattern increasing the concentration of the capture reagent from a leading boundary to the trailing boundary of the detection zone.

34. The method claim 30 wherein the immobilizing step includes depositing the capture reagent in a predetermined pattern of a plurality of stripes extending across the width of the detection zone.

35. The method of claim 34 wherein the depositing step includes increasing the amount of the capture reagent in each successive stripe of the plurality from the leading boundary to the trailing boundary of the detection zone.

36. The method of claim 34 wherein the depositing step includes overlapping the plurality of stripes in a cascade pattern to form areas successively increasing the concentration of capture reagent from the leading boundary to the trailing boundary.

37. The method of claim 30 wherein the distributing step includes forming a uniform distribution of capture efficiency yielding the physically detectable change wherein the capture efficiency effectively changes at a constant rate across the detection zone to present a uniform gradient.

38. The method in claim 37 wherein the forming step includes:

diffusively immobilizing a blocking agent on the transport strip prior to the detection zone;

transporting the blocking reagent across the detection zone to form the uniform distribution of capture efficiency yielding the physically detectable change.

39. The method in claim 38 wherein the transporting step includes transporting the blocking reagent across the detection zone simultaneously with the sample.

40. The method in claim 38 wherein the transporting step includes transporting the blocking reagent across the detection zone prior to transporting the sample across the detection.

41. The method in claim 37 wherein the forming step includes the steps of:

depositing a capture reagent in a uniform pattern from the leading boundary to the trailing boundary of the detection zone;

immobilizing a blocking agent in a predetermined distribution within the detection zone with capture reagent to prevent at least a portion of the capture reagent from reacting further to form the uniform distribution of capture efficiency yielding the physically detectable change.

42. The method of claim 41 wherein the immobilizing step includes binding the blocking reagent with the capture reagent to prevent at least a portion of the capture reagent binding with the analyte or signal producing conjugate.

43. The method of claim 41 wherein the immobilizing step includes binding the blocking reagent with the analyte or signal producing conjugate to prevent at least a portion of the analyte or signal producing reagent from binding with the capture reagent.

44. The method of claim 30 wherein the method further includes the steps of:

determining the analyte level in the sample by combining the response from at least two detection zones;

non-diffusively immobilizing a trap reagent on the transport matrix before the final detection zone, the trap reagent present in an amount effective to immobilize analyte in excess of the capture capacity of the prior detection zone.

45. The method of claim 30 wherein the method further includes the step of depositing a diffusion control material across the detection zone, the diffusion control material slowing the transportation of the sample across the detection zone and increasing capture efficiency of the capture reagent from the leading boundary to the trailing boundary of the detection zone.

* * * * *